United States Patent [19]

Henklein et al.

[11] Patent Number: 4,714,768

[45] Date of Patent: Dec. 22, 1987

[54] N-(CHLOROCARBONYLOXY)-5-NORBOR-NENE-2,3-DICARBOXIMIDE, PROCESS FOR ITS PRODUCTION AND ITS USE

[75] Inventors: Peter Henklein; Manfred Becker; Werner Büttner, all of Berlin; Fritz Loth; Horts Dautzenberg, both of Teltow; Klaus Forner; Rudolf Dölling, both of Berlin; Karl-Heinz Graul, Quedlinburg; Wolf-Rainer Halatsch, Glienicke; Christian Rupprich, Berlin, all of German Democratic Rep.

[73] Assignee: Akademie Der Wissenschaften Der DDR, Berlin, German Democratic Rep.

[21] Appl. No.: 644,777

[22] Filed: Aug. 27, 1984

[30] Foreign Application Priority Data

| Aug. 25, 1983 [DD] | German Democratic Rep. ..................... 2541961 |
| Aug. 25, 1983 [DD] | German Democratic Rep. ..................... 2541978 |
| Aug. 25, 1983 [DD] | German Democratic Rep. ..................... 2541986 |
| Oct. 28, 1983 [DD] | German Democratic Rep. ..................... 2560562 |
| Oct. 28, 1983 [DD] | German Democratic Rep. ..................... 2560570 |

[51] Int. Cl.$^4$ ............................................. C07D 209/02
[52] U.S. Cl. ............................................. 548/435; 525/59; 525/282; 530/335; 530/337; 530/402; 530/403
[58] Field of Search .......................................... 548/435

[56] References Cited

U.S. PATENT DOCUMENTS

| 2,872,450 | 2/1959 | Sasse et al. .................. 548/475 X |
| 4,010,178 | 3/1977 | Kamiya et al. ................ 558/262 X |
| 4,341,707 | 7/1982 | Ogura et al. ................. 558/262 X |

OTHER PUBLICATIONS

March, ed., Advanced Organic Chemistry, 2nd ed., McGraw-Hill (1977), pp. 361–362.

Primary Examiner—Donald G. Daus
Assistant Examiner—William A. Teol, Jr.
Attorney, Agent, or Firm—Michael J. Striker

[57] ABSTRACT

A new compound is disclosed, N-(chlorocarbonyloxy-5-norbornene-2,3-dicarboximide I, in addition to processes for its production and employment of the compound as starting product for the manufacture of non-symmetrical carbonate, urethane-protected amino acid or peptide, activated carrier and carrier-ligand-complexes. The new compound is reacted with alcohols as well as with hydroxyl-group-containing or amino-group-containing polymers.

1 Claim, No Drawings

N-(CHLOROCARBONYLOXY)-5-NORBORNENE-2,3-DICARBOXIMIDE, PROCESS FOR ITS PRODUCTION AND ITS USE

BACKGROUND OF THE INVENTION

The invention concerns N-(chlorocarbonyloxy)-5-norbornene-2,3-dicarboximide I, processes for its production as well as its use. The compound I is new. It represents an important intermediate product for the manufacture of non-symmetrical carbonates and activated polymeric carriers. The utility of the present invention lies in the pharmaceutical and chemical industries, as well as in biotechnology.

Chloroformic acid esters are known to be compounds of great preparative significance. For the production from phosgene and the hydroxyl compounds, three processes are employed. In the most important process, phosgene is reacted directly with the alcohols (B. Roge, Liebigs Ann. Chem. 205, 227 (1880); Houben-Weyl, 4. Aufl. (1952), Bd. 8, S. 101 bis 102; US-PS 2476 637). For this purpose, either liquid phosgene or a phosgene in an inert organic solvent (toluene) is provided, and the alcohol is added dropwise. (W. Hentschel, Chem. Bericht 18, 1177 [1885]) or the reverse, phosgene is lead through cooled alcohol. (C. Hamilton, C. Sly, Amer. Chem. Soc. 47, 436 [1925]). According to another technique, one works with tertiary amines, and the hydrogen chloride produced during the reaction is supposed to be collected. As tertiary amine, e.g., dimethylaniline or pyridine is used. These processes are suitable mainly for the production of aromatic chloroformic acid ester. In other techniques for the aromatic chloroformic acid esters, alkali phenolates are mentioned for hydrogen chloride binding with the reaction with phosgene. These techniques follow in inert solvents (K. V. Anwers, W. Scheich, Chem. Ber. 54, 1969 [1921]), or even in aqueous organic solvent systems (E. Barrat, A. Morel, Comptes Rendus Hebdomadaires des Séances de l'Académie des Sciences 128, 1578 [1899]).

The chloroformic acid esters of 9-fluorenylmethanol, of pentachlorophenol, of benzotriazol and of N-hydroxysuccinimide are important as initial products for protective groups in the synthesis of peptide (A. Paquet, Can. J. Chem. 60, 976 [1982]). However, the obtained chloroformic acid esters, limited by their low hydrolysis stability or too low aminolysis velocity are not advantageously useful. A plurality of symmetrical carbonates is moreover, known which are employed for the introduction of urethane protective groups in amino acids. The tert.-butyloxycarbonyl-(BOC)-group represents, in addition to the benzyloxycarbonyl-(Z)-group, the most frequently employed protected group in the peptide synthesis. In order to avoid the disadvantages of high toxicity and explosion tendency possessed by the previously mainly employed BOC-introduction reagents tert.butyloxycarbonyloxide (Schwyzer, R., Sieber, P. and Keppler, H., Helv. Chim. Acta 42, 2622 [1962]), new introduction reagents have been developed in great number, such as tert.-butyl-4-,6-dimethylpyrimidyl-2-thiol-carbonate (Hagasawa, T., Kuriowa, K., Nerite, K. and Isowa, Y., Bull Chem. Soc. [Jap.] 46, 1269 [1973], and A. C. McGregor, J. Amer. Chem Soc. 72, 6180 [1957]); tert.-butyloxycarbonyloxyimino-2-phenylacetonitrile (Itoch., H., Hagiwara, D. and Kamiya, T., Bull. Chem. Soc. [Jap.] 50, 718 [1977]; Tetrahedron Lett. 1975, 4393; N-(tert.butyloxycarbonyloxy)-phthalimide (Gross, N. and Bilk, L. Liebigs Ann. Chem. 725, 212 [1969]); N-(tert.-butyloxycarbonyloxy)-succinimide (Franket, M., Ledkeny, D., Gilon, C. and Wolamn, Y., Tetrahedron Lett. 1966, 4765; Gross, H. and Bilk, L., Liebigs. Ann. Chem. 725, 212 [1969], N-(tert.-butyloxycarbonyl)-1H-1,2,4-triazol (G. Bram, Tetrahedron Lett. 1973, 469), tert.-butyl-phenylcarbonate (Ragnarsson, U., Karlson, S. M., and Sandberg, B. E., Acta Ehcm. Scand. 26, 2550, [1972]; Org. Synth. 53, 25 [1973]); tert.-buty-S-quinolycarbonate (Rzesztotarska, B. and Wiejak, S., Liebigs Ann. Chem. 716, 216 [1968]; Rzesxtotarska, B., Wiejak, S. and Pawelozak, K., Org. Prep. Proc. Int. 5, 71 [1973]); tert.-butyl-2,4,5-trichlorophenylcarbonate (Broadbent, W., Morley I. S., and Stone, B. E., J. Chem. Soc. (C), 1967, 2632) and Di-tert.-butyl-dicarbonate (Tarbell, D. S., Yamamoto, Y. and Pope, B. M., Proc. Nat. Acad. Sci. USA 69, 730 [1972]; Org. Synth. 57, 45 [1977]; Moroder, L., Hallet, A., Wunsch, E., Keller, O. and Wersin, G., Hoppe-Seyloer's Z. Physiol. Chem. 357, 1651 [1976]).

In addition to these frequently employed protective groups, further significant protective groups are required for specific synthesis problems. In this connection, in recent years, mainly such compounds have been approved which can be split off under milder conditions. These include, e.g., the 9-fluoroenylmethyloxycarbonyl-group (Carpino, L., J. Amer. Chem. Soc. 92, 5748 [1970]), the methylsulfonylethoxycarbonyl-group (G. Tesser et al., Intern. J. Peptide Prot. Res. 7, 295 (1975) or 1-adamantyloxycarbonyl-protective group (E. Wunsch, L. Wackerle and L. Moroder, Hoppe-Seylers Z. Physiol. Chem. 357, 1647 [1976]). All of these last mentioned protective groups are usually introduced across substituted phenol or H-hydroxysuccinimide ester (M. Bodanszky, Y. S. Klausner and M. A. Ondetti in: Peptide Synthesis, 2nd ed., J. Wiley & Sons, N.Y., 1976, p. 32; H. Gross and L. Bilk, Liebigs Ann. Chem. 725, 212 [1969]; A. Paquet, Can. J. Chem. 57, 2775 [1979] and Can. J. Chem. 60 (8) [1982]).

The mentioned introduction reagents distinguish by the remarkably high yields of urethane-protected amino acids that are obtained. Their disadvantage, however, for the most part, is that with the majority of them, not only the synthesis of the starting material but also the manufacture of the introduction reagent, is connected with high preparative and technical expenditure and their storage stability is limited. Moreover, often the aminolysis velocity is limited.

Also known are so-called carrier-fixed reagents, which are employed during material transformation processes or analytical and preparative material separations. (A. Wisemann, ed., Handbood of Enzyme Chemistry, New York, 1975, D. R. Lowe: "An Introduction to Affinity Chromatography", Amsterdam, 1979.) The carrier-fixed system is composed of the polymeric matrix, the carrier, in which by means of covalent or adsorptive binding, the material with the desired specifc activity (ligands) are connected. Natural or synthetic compounds with determined chemical or biological activity are employed as ligands, e.g., enzyme as catalyst for material transformation, protein and peptide with the activity of lectines, inhibitors, antigens or antibodies, nucleic acids, polysaccharides, sugar-derivatives, among others. The polymers employed for the binding of the ligands are natural polysaccharides such as, e.g., cellulose, starch, dextrane, agarose and their derivatives, or synthetic, hydroxyl group-containing polymers such as mixed polymerizate of 2-hydroxylethylmethacrylate (Spheron) or phenol-formaldehyde condensate (Duolite) as well as amino group-containing polyers such as polyacrylamide, modified polysaccharide (e.g., AH-Sepharose) or even proteins.

The manner of forming covalent bindings between carriers and ligands exerts a substantial influence on the characteristics of the produced product, and is therefore always the subject of renewed investigations. Most frequently, the binding of peptide-like ligands follows across their accessible alpha- and epsilon-amino groups, although the possibility also exists for reaction of the carboxyl group or the SH group. Prerequisite for the binding of the ligands is the activation of the chemically slightly reactive hydroxyl groups of the carrier.

Of many possible activation methods the reaction of the polysaccharide into cyanate or imidocarbonate is mainly performed in practice by means of cyanogenbromide, although a series of disadvantages is attached to it (i.e., the reaction of the CNBr-activated carrier with amino groups leads to isourea derivatives which can maintain the character of weak ion exchangers; and high toxicity of the bromocyanogen and its hydrolysis products).

An activation of the hydroxyl groups has furthermore, been described with benzoquinone, divinyl sulfone, diepoxide, trichlorotriazine and other bifunctional reagents, as well as the oxidation of the hydroxyl groups into aldehyde functions by means of sodium periodate.

A promising alternative to the activation with bromocyanogen is seen in the reaction of polysaccharides with chloroformic acid esters.

In the case of the reaction of the chloroformic acid ethyl ester with cellulose (S. A. Barker, Carbohydr. Res. 17, 471 [1971]), the formation of trans-2,3-cyclical carbonate and O-ethoxycarbonyl functions has been described, which react with amino groups. The binding of several enzymes and the manufacture of immunoadsorbants is known. (C. H. Grey, Carbohydr. Res. 27, 235 [1973]; J. F. Kennedy, J. Immunol. Meth. 50, 57 [1982]).

The high toxicity and the extreme hydrolysis sensitivity of this chloroformic acid ester are the main disadvantages of this activation. Seen to be advantageous compared to the activation with bromocyanogen is the high stability of the noncharged urethane-compounds arising by means of reaction with amino functions. The usefulness of the method is clearly improved through insertion of more reactionable and more hydrolysis-resistant chloroformic acid esters, which are employed in peptide chemistry. The Sepharose, Spheron and cellulose carriers activated by means of chloroformic acid-p-nitrophenyl ester, chloroformic acid-N-hydroxysuccinimide ester or chloroformic acid-trichlorophenyl ester are stable in the dry state or in water-free dioxane. (J. Drobnik, Biotechnol. Bioeng. 24, 487 [1982]; M. Wilchek and T. Miron, Biochem. Internat. 4, 629 [1982]).

Characteristics that are decisive for the practical usefulness are the high chemical and storage stability of the activated carrier and of the chloroformic acid ester employed for the production. Whereas the stability of the previously described activated carriers has been satisfactory, not only chloroformic acid ethyl ester but also chloroformic acid-N-hydroxysuccinimide ester are difficultly handleable on account of their high hydrolysis sensitivity, particularly when they are supposed to be worked up in greater scale. Disadvantages of the chloroformic acid-phenyl ester derivatives exist in that the separation of the most poisonous phenols produced upon the reaction with amino functions is difficult, but must nevertheless follow very thoroughly since they frequently disturb the biological activity of the systems investigated. Accordingly, protracted washing of the manufactured carrier-fixed enzymes, among others, is necessary.

The methods useful for the immobilization of the most diverse ligands in polymeric carriers are described in reviews and monographs. (Chemical Analysis, Vol. 59, P. J. Elving and J. D. Winefordner, eds., New York, 1981; E. A. Hill, M. D. Hirtenstein, in Advances in Biotechnological Processes 1, pp. 31–66, New York, 1983.)

SUMMARY OF THE INVENTION

The aim of the present invention is to make available a new, stable initial product suitable for advantageous manufacture of non-symmetrical carbonates, which for their part can be used for the introduction of urethane-protected groups in amino acids and which further make possible the simple and economical preparation of activated carriers for the binding of nucleophilic components as well as more stable carrier-ligand-complexes.

The invention is therefore based upon the object of developing the initial product, processes for its production as well as its use whereby the inventive aim can be realized. This object has been met according to the present invention by preparation of the new chloroformic acid ester N-(chlorocarbonyloxy)-5-norbornene-2,3-dicarboximide (Cl-CO-ONB) I. By means of reaction of phosgene with N-hydroxy-5-norbornene-2,3-dicarboximide (HONB) II or with the sodium salt of the N-Hydroxy compound (NaONB) III is the desired compound Cl-CO-ONB I obtained (formula scheme 1). The non-symmetrical carbonates IV in which $R^1$ stands for tert.-butyl, adamantyl-(1), 2-diphenylpropyl, 9-methylfluoroenyl, methylsulfonylethyl, benzyl or other groups customary in peptide chemistry (formulae schemes 1 and 2) can be recovered from the Cl—CO—ONB I prepared according to the invention with the corresponding alcohols (Table 1). By means of reaction with amino acids or peptides which contain an unprotected amino group, urethane-protected amino acids or peptides V (formula scheme 1) in which $R^2$ stands for amino acid or peptide group (Table 2), are obtained from the non-symmetrical carbonates IV.

Employment of the chloroformic acid ester I for preparation of the activated carrier of formulae VII and X follows in that I is reacted with hydroxyl-group-containing polymers of the formula VI or amino-group-containing insoluble polymers of formula IX in which $R^4$ stands for $NH_3$-alkyl, substituted alkyl, aryl or substituted aryl (formula scheme 1). The produced activated carrier VII is thereby characterized in that the accessible hydroxyl groups are substituted to a widely variable extent by the —O—CO—ONB grouping, respectively the amino groups of carrier IX are substituted by the grouping —NH—CO—ONB.

The reaction of carrier VI and IX with the compound I follows in water-free organic solvent, such as 1,4-dioxane, acetone, pyridine, ether, among others. By means of washing the produced product with dioxane, ether or acetone, non-reacted N-(chlorocarbonyloxy)-5-norbornene-2,3-dicarboximide I and released hydrogen chloride are removed.

In general, the reaction runs in the same manner when the transformation is performed in the presence of tertiary amine for binding of the produced hydrogen chloride. The advantage of the addition of base is to be seen in that the solution of chloroformic acid ester I, separated from the activated carrier by means of filtration, can be employed anew for the reaction with the carrier, without thereby lowering the activation rate. By means of the repeated employment of the solution of chloroformic acid ester I, the economy of the activation technique is considerably improved. The activated carrier can be stored, after removal of the solvent, in the dry state or in a water-free solvent such as dioxane, ether, chloroform, among others, at low temperature and over a period of months without loss of activity. The carrier obtained by reaction with I is also extensively stable in aqueous solution.

The advantage of the activated carrier obtained according to the present invention is its higher stability in alkaline milieu. By means of the low hydrolysis velocity of the activated carrier it is possible to undertake the coupling with nucleophilic reagents at comparatively high pH values.

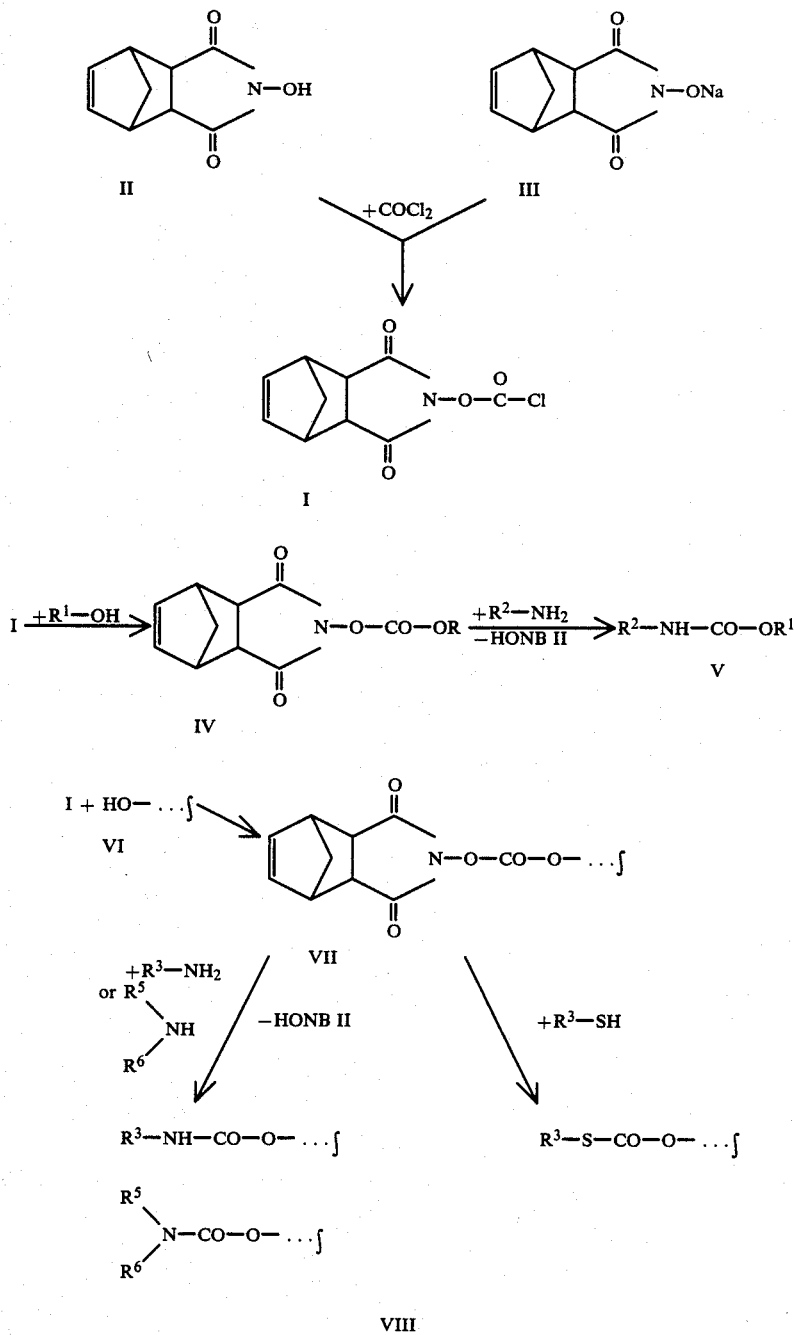

Formula Scheme 1

Formula Scheme 1

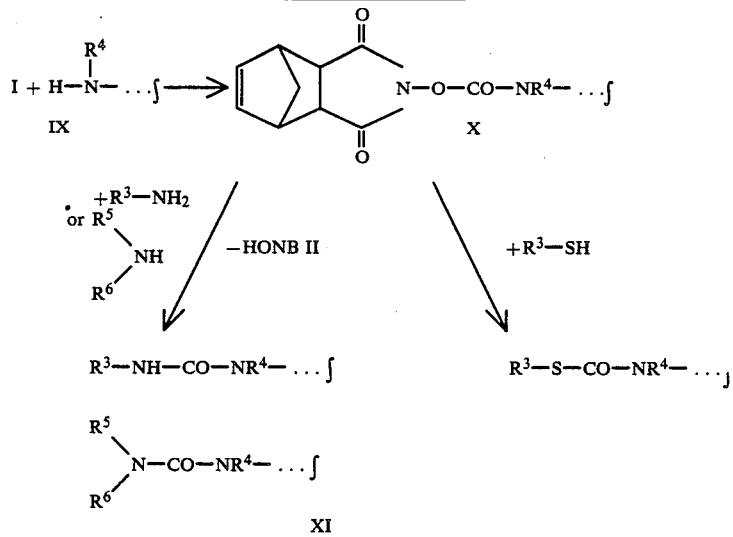

Formula Scheme 2

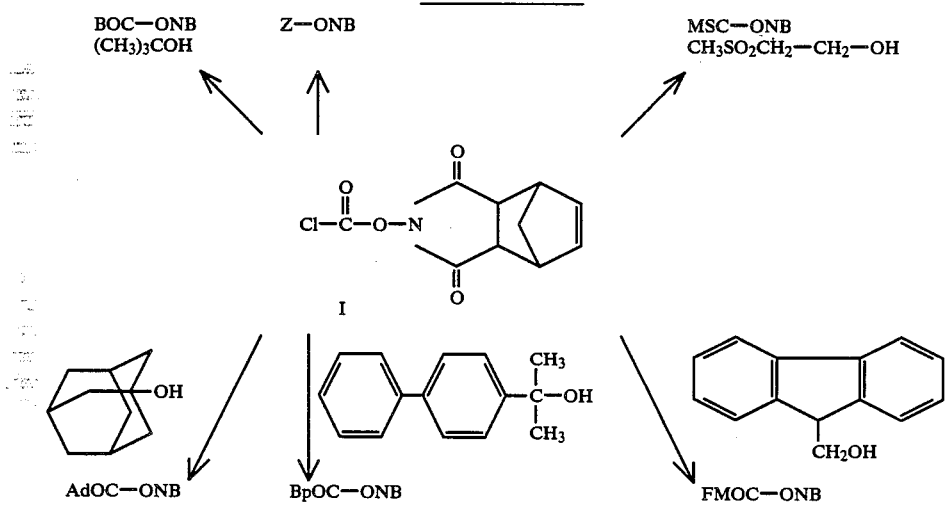

As hydroxyl-group-containing carriers of formula VI, natural polysaccharides, such as cellulose in the most different forms, starch, starch hydrolysis product (SHP), cross-linked dextrane and agarose as well as synthetic polymers, such as polyvinyl alcohol (PVA), Duolite, Spheron, hydrophilic vinyl polymers (Fractogel TSK) among others, and even inorganic carriers, such as e.g., porous glass, can be employed. Moreover, also amino-group-containing insoluble polymers of formula IX, such as e.g., aminoalkylcellulose, aminoalkylpolystyrene, melamine and urea-formaldehyde resin and polyacrylamide can be employed as carrier.

An additional advantage exists in the easy accessibility of the employed chloroformic acid ester I, the good storage stability of the activated carrier, which allows for reaction on a greater scale. It is to be emphasized that the ester solution I employed in excess can be utilized many times for the reaction, without renewed purification. Losses of yield with regard to the activated carriers are not perceptible.

The so obtained carriers distinguish by a high reaction velocity upon conversion with amino group- and SH-group-containing ligands (formula scheme 1). The carrier-ligand-complexes of formulae VIII and XI produced by the reaction with nucelophiles, in which $R^3$ is alkyl, substituted alkyl, aryl, substituted aryl, $R^3$-$NH_2$ is peptide or protein, and $R^5$ as well as $R^6$, are alkyl, substituted alkyl, aryl, substituted aryl, display a high stability. An advantage of the immobilization of the ligands is that the N-hydroxy-5-norbornene-2,3-dicarboximide (HONB) II produced with the coupling can be easily removed as a result of its very good water solubility. A further advantage, in contrast to the hydroxysuccinimide esters, is that upon the hydrolysis of chloroformic acid ester-activated polymers, no charged groups are produced, but the originally present hydroxyl groups of the carriers are re-formed. Compared to the previously employed chloroformic acid esters, the hydrolysis of the polymers activated with the compounds I is less pronounced. In this manner one succeeds in eliminating the disadvantages of the previously known methods for the production of carrier-ligand-complexes. By means of employment of suitable groups $R^3$, such as e.g., $CH_2$—$CH_2$—$N(R^7)_2$ with $R_7$=H, $CH_3$, $C_2H_5$, ($CH_2$—$CH_2$—NH)$_n$H with N=1 to 500, C(NH)—$NH_2$, $C_6H_4$—$NH_2$ or $CH_2$—COOH, Cl—CO—ONB I is also suitable for the manufacture of ion exchangers.

Therewith the invention concerns compound Cl—CO—ONB I, processes for its production, the employment of the compound I as initial product for the manufacture of non-symmetrical carbonate of formula IV, urethane-protected amino acids or peptides of formula V, activated carriers of formulae VII and X and of carrier ligand-complexes of formulae VIII and XI, which moreover are useful as ion exchangers. The compound I obtained according to the present invention itself or intermediate products prepared from it serve as means for preparation of the mentioned products. The process for preparation of these means are thereby characterized in that Cl—CO—ONB I is reacted with alcohol of the formula $R^1$—OH, with hydroxyl-group-containing carriers VI or with $NH_2$-group-containing polymers into the desired product or into intermediate products. The non-symmetrical carbonates IV can be prepared also without isolation of the Cl—CO—ONB I after the reaction of HONB II with phosgene in a so-called one-pot process. The reaction of hydroxyl-containing carriers VI, such as cellulose, e.g., in the form of paper, fibers, powder and beads, moreover, starch hydrolysis product (SHP), cross-linked dextrane, agarose and polyvinyl alcohol, Duolite, Fractogel or Spherone with I follows in water-free organic solvents, if necessary in the presence of base. By means of washing of the produced activated carrier, non-reacted compounds I and released hydrogen chloride are removed, whereby the ester solution I can be employed many times for the reaction without renewed purification. The activated carrier is stored in water-free solvent or in lyophilized form. In analogous manner follows the reaction of amino-group-containing polymeric carriers IX with the ester I. The carrier ligand-complex of formulae VIII and XI are formed by means of covalent binding of nucleophilic ligands in hydroxyl-group-containing compounds activated by means of Cl—CO—ONB I, such as natural polysaccharides, agarose, dextrane, cellulose, e.g., paper, cellulose powder and beads, starch and starch hydrolysis products (SHP), chemically modified polysaccharides and synthetic polymers, such as polyvinyl alcohol, Duolite, Spherone among others, and oligomers or amino-group-containing insoluble polymers, such as e.g., aminoalkylcellulose, aminoalkylated, polystyrene, ureaformaldehyde and melamine-formaldehyde resin or polyacrylamide. Useful as nucleophilic ligands are proteins, enzymes, nucleic acids, amino acids, nucleotides, antigens and antibodies, hormones, receptors, SH-group-containing compounds and amines. The HONB II produced upon the reaction of the carrier and ligand is removed by means of washing with aqueous solvent.

The novel features which are considered as characteristic of the invention are set forth in particular in the appended claims. The invention itself, however, both as to its construction and its method of operation, together with additional objects and advantages thereof, will be best understood from the following description of specific embodiments.

| LIST OF ABBREVIATIONS | |
|---|---|
| Adoc—ONB | adamantyl-(1)-oxycarbonyl-ONB |

-continued

| LIST OF ABBREVIATIONS | |
|---|---|
| AS | amino acid |
| Boc—ONB | tertiary-butyloxycarbonyl-ONB |
| Bpoc—ONB | 2-diphenylpropyloxycarbonyl-ONB |
| Cl—CO—ONB | N—(chlorocarbonyloxy)-5-norbornene-2,3-dicarboximide |
| Fmoc—ONB | 9-fluoroenylmethyloxycarbonyl-ONB |
| HONB | N—hydroxy-5-norborene-2,3-dicarboximide |
| Mac—ONB | methylsulfonylethyloxycarbonyl-ONB |
| NaONB | sodium salt of HONB |
| —ONB | —oxy-5-norbornene-2,3-dicarboximide |
| SHP | starch hydrolysis product |
| THF | tetrahydrofuran |
| TNBS | trinitrobenzenesulfonic acid |
| Z—ONB | benzyloxycarbonyl-ONB |

EXAMPLE 1

Preparation of N-(chlorocarbonyloxy)-5-norbornene-2,3-dicarboximide

EXAMPLE 1.1

A solution composed of 17.9 g HONB, 12 g N,N-dimethylaniline in THF/benzene (about 200 ml) is added dropwise to a solution of phosgene (9.9 g; 0.1 mol) at a temperature from 0°–5° C. The mixture is then stirred for one hour at this temperature, allowed to stand overnight, and then the hydro chloride is separated and the solvent is evaporated in a vacuum. The solid residue is withdrawn in 50 ml THF, which is then cooled to $-20°$ C., filtered and compressed again in a vacuum.

F.=98°–100° C. (decompositon)
Yield: 95%
Molpeak at 241
IR (1740 $cm^{-1}$ CL—CO; 1800 $cm^{-1}$, 1820 $cm^{-1}$ imidocarbonyl)

EXAMPLE 1.2

9.9 g (55 mMol) of HONB are reacted with 55 ml methanolic 1N NaOH. After a brief period, the Na-salt begins to precipitate. The precipitation of the Na-salt is completed by an addition of 100 ml diethyl ether. The salt is evaporated in a vacuum and then dried across $P_4O_{10}$. Yield: 9.85 g.

9.85 g of the dried Na-salt are added portionwise and with stirring to a solution of 55 mMol phosgene in 200 ml toluene at room temperature. The mixture is further stirred overnight, whereupon precipitated NaCl is filtered off. The filtrate is compressed and then the remaining solid is withdrawn in a little THF (50 ml). The solvent is separated again in a vacuum. The remaining solid is identical to the product obtained under Example 1.1.

EXAMPLE 2

Preparation of Non-symmetrical Carbonate IV

EXAMPLE 2.1

0.1 mol N-chlorocarbonyloxy-5-norbornene-2,3-dicarboximide (Cl-CO-ONB) I is dissolved in 150 ml of an inert solvent (e.g., toluene, benzene, THF, halogenated hydrocarbon) and at a temperature between 10°–15° C. a solution of 0.1 mol of an alcohol (Table 1) and 0.1 mol of a tertiary amine in 40 ml of an inert solvent (as mentioned above) is added. The mixture is then stirred for one hour at room temperature and for three hours at a temperature of 35° C. It is then allowed to stand overnight. The sediment, composed of amine-hydrochloride, is separated, and the filtrate is compressed. For separation of the remainder of the amine, it is also possible to wash the solution, before compressing, with ice-cold 5% NaHCO$_3$ (Table 1).

EXAMPLE 2.2

A solution composed of 17.9 g HONB, 12 g N,N-dimethylaniline in THF/benzene (about 200 ml) is added dropwise to a solution of phosgene (9.9 g; 0.1 mol) at 0°–5° C. The mixture is then stirred at this temperature for one hour and allowed to stand overnight. It is further processed without isolation of the Cl-CO-ONB as specified under Example 2.1.

EXAMPLE 4.1

14 ml ester solution Cl-CO-ONB I (concentration 38 mg/ml) is added to 1 ml of pearl cellulose sedimented in water-free dioxane. The suspension is agitated a few hours at 60° C. The filtered-off carrier is washed with water-free dioxane and then reacted with 5 ml glycine solution (concentration 4 mg/ml=53.4 μMol/ml) in 0.1M Na-tetraborate buffer pH8. After two hours agitation at room temperature, the carrier is separated by suction filtration and the glycine consumption is determined.

Results: 49.3 μMol glycine/ml carrier

TABLE 1

Non-symmetrical Carbonate

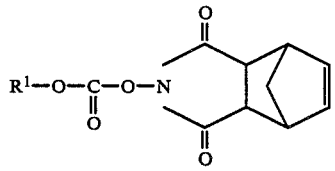

IV

| R$^1$ | Fp. °C. | Mol mass | Formula | Element Analysis Cal. Fd. | C C | H H | N N | MS (M$^+$) |
|---|---|---|---|---|---|---|---|---|
| Adamantyl | 220 | 357.1 | C$_{20}$H$_{23}$NO$_5$ | | 67.21 67.43 | 6.49 6.52 | 3.92 3.87 | 357.1 |
| Tert.-butyl | 124 | 279.3 | C$_{14}$H$_{17}$NO$_5$ | | 60.20 60.50 | 6.10 6.07 | 5.01 5.17 | 279.3 |
| 9-methylfluoroenyl | 129 | 401.1 | C$_{24}$H$_{19}$NO$_5$ | | 71.81 71.7 | 4.77 4.5 | 3.49 3.57 | 401.4 |
| CH$_3$—SCH$_2$—CH$_2$ | 145 | 313.26 | C$_{13}$H$_{15}$NO$_6$S | | 49.84 49.87 | 4.83 4.73 | 4.47 4.31 | 313 |
| 2-biphenyl-propyl | 121 | 417.4 | C$_{25}$H$_{23}$NO$_5$ | | 71.99 71.80 | 5.55 5.42 | 3.36 3.21 | 417.4 |

EXAMPLE 3

Preparation of Urethane-protected Amino Acid and Peptide V

The respective amino acid is dissolved in a mixture of water/acetone, water/dioxane or water/t-butanol (possibly suspended) and then reacted with the two-to-four-fold molar amount of triethylamine. In connection therewith the non-symmetrical carbonate IV is added in an excess of 10%. The mixture is then stirred at room temperature for several hours (the reaction temperature amounting to 45° C., depending upon the amino acid, upon introduction of the Bpoc-protective groups). The organic solvent portion is removed in a vacuum and the remaining residue is acidified with 10% KHSO$_4$.

One then distributes between methylene chloride and KHSO$_4$-solution, followed by separation of the organic phase. The organic phase is washed thoroughly with water for removal of the residual HONB, and then dried across MgO$_4$. It is then compressed and triturated with N-hexane (Table 2).

EXAMPLE 4

Preparation of Activated Carrier VII

The covalent binding of glycine is determined after the activation step as a result of an activation of the carrier. The consumption of added glycine is determined according to the TNBS-method (trinitrobenzene sulfonic acid, reagent for NH$_2$ groups).

TABLE 2

| Urethane-protected Amino Acid resp. Peptide | Derivative AA/Peptide | Fp.(°C.) | Yield (%) |
|---|---|---|---|
| 1. Boc—ONB | Boc—Ala—OH | 82 | 87 |
| | Boc—Gly—OH | 85–87 | 85 |
| | Boc—Leu—OH | 79–83 | 91 |
| | Boc—Pro—OH | 132–33 | 88 |
| | Boc—Trp—OH | 136–38 | 86 |
| | Boc—β-Ala—OH | 79–81 | 84 |
| | Boc—Phe—OH | 82–84 | 91 |
| 2. Fmoc—ONB | Fmoc—Ala—OH | 144 | 95 |
| | Fmoc—Gly—OH | 172–74 | 87 |
| | Fmoc—Leu—OH | 153–55 | 91 |
| | Fmoc—Phe—OH | 180–82 | 95 |
| | Fmoc—Val—OH | 142–44 | 85 |
| | Fmoc—Ser—OH | 86–88 | 87 |
| | Fmoc—Trp—Met—OH | 138 | 79 |
| | Fmoc—Met—Gly—OH | 110–112 | 77 |
| 3. Adoc—ONB | Adoc—Phe—OH | 60–65 | 82 |
| | Adoc—Ala—OH | 140–41 | 84 |
| | Adoc—Gly—OH | 141–42 | 87 |
| 4. Bpoc—ONB | Bpoc—Pro—OH | 122–124 | 81 |
| | Bpoc—Pro—OH | 85–87 | 85 |
| 5. Msc—ONB | Msc—Phe—OH | 112–113 | 89 |
| | Msc—Ile—OH | 92–95 | 81 |

EXAMPLE 4.2

Sepharose 4 B CL is activated in the same manner as detailed in Example 4.1. It is then treated with glycine solution, also according to the same technique.

Yield: 33.3 μMol glycine/ml carrier.

EXAMPLE 4.3

Spherone P 1000 is activated in the same manner as detailed in Example 4.1, and then treated with glycine solution, also according to the same technique.

Yield: 49.3 μMol glycine/ml carrier.

EXAMPLE 4.4

Pearl cellulose (bead cellulose) is activated at a temperature of 80° C. while maintaining all of the other conditions set forth in Example 4.1, including the coupling with glycine.

Yield: 69.3 μMol glycine/ml carrier.

EXAMPLE 4.5

Pearl cellulose is activated as described in Example 4.1, whereby 10 mg triethylamine as base, per ml carrier, is added to the ester solution I. The coupling with glycine is then performed as described in Example 4.1.

Yield: 31.3 μMol glycine/ml carrier.

EXAMPLE 4.6

The ester solution recovered from Example 4.5 is employed again for activation (with conditions as described in Example 4.5, under repeated addition of base to the ester solution, 10 mg/ml carrier).

Yield: 56.0 μMol glycine/carrier.

EXAMPLE 4.7

1 ml pearl cellulose, suspended in water-free dioxane, is agitated for six hours at 80° C. with 3.5 ml ester solution I (concentration 200 mg/ml). After filtering and washing with water-free dioxane, the carrier is reacted with 5 ml glycine solution (concentration 4 mg/ml=53.4 μMol/ml) in 0.1M Na-tetraborate buffer pH8. The suspension is agitated, first for two hours at room temperature, and then at 22 hours at 4° C.

Yield: 116 μMol glycine/ml carrier.

EXAMPLE 4.8

1 ml pearl cellulose, suspended in water-free dioxane, is agitated for a period of three hours at a temperature of 70° C. with 1.7 ml ester solution (concentration 300 mg/ml). After filtration and washing of the carrier with water-free dioxane, 5 ml glycine solution (concentration 4 mg/ml=53.4 μMol/ml) in 0.1M phosphate buffer pH8 are added, followed by agitation at room temperature for two hours.

Yield: 116.7 μMol glycine/ml carrier.

EXAMPLE 4.9

1 ml pearl cellulose is treated as described in Example 4.8. The glycine is added in 0.5M $NaHCO_3$, and the coupling is performed for 24 hours at 4° C.

Yield: 150.7 μMol glycine/ml carrier.

EXAMPLE 4.10

100 mg cellulose (dry) are activated with 30 ml ester solution I (concentration 37 mg/ml) for three hours at 60° C. Coupling with glycine follows for two hours at room temperature with 10 ml solution (concentration 4 mg glycine/ml 0.1M Na-tetraborate buffer pH8) under mild agitation.

Yield: 63.7 μMol glycine/100 mg cellulose.

EXAMPLE 5

Preparation of Carrier-ligand-complex VIII

As an example of ligand binding, the coupling of ovomucoid and concanavalin A (ConA) is performed, whereby the amount of bound protein is determined after 18 hours treatment of the carrier with 1M NaOH according to Lowry et al., J. of Biol. Chem. 193, 265 (1951).

EXAMPLE 5.1

14 ml ester solution Cl-CO-ONB I (concentration 38 mg/ml) are added to 1 ml pearl cellulose suspended in water-free dioxane. The suspension is then agitated for three hours at 60° C. The filtered-off carrier is washed with water-free dioxane and then reacted with 1.2 ml ovomucoid solution in 0.1M Na-tetraborate buffer pH8 (ovomucoid addition, 10 mg/ml carrier).

The coupling is performed for two hours at room temperature, with agitation.

Yield: 1.24 mg ovomucoid/ml carrier.

EXAMPLE 5.2

The same tests as in Example 5.1 are performed with Sepharose 4 B CL.

Yield: 2.48 mg ovomucoid/ml carrier.

EXAMPLE 5.3

The same tests as in Example 5.1 are performed with Spherone P 1000.

Yield: 1.45 mg ovomucoid/ml carrier.

EXAMPLE 5.4

The test is performed as described in Example 5.1, however an ovomucoid addition of 100 mg/ml carrier is employed.

Yield: 18.6 mg ovomucoid/ml carrier.

EXAMPLE 5.5

The test is performed as described in Example 5.1, however the ovomucoid coupling follows at room temperature for two hours, and then at 4° C. for an additional 24 hours.

Yield: 7 mg ovomucoid/ml carrier.

EXAMPLE 5.6

The test is performed as described in Example 5.1. The activation conditions are altered as follows: six hours at 80° C. with 3.5 ml ester solution I (concentration 200 mg/ml per ml pearl cellulose). Coupling follows by means of addition of 1.2 ml ovomucoid solution (concentration 41.66 mg ovomucoid/ml) and agitation for two hours at room temperature, followed by 22 hours at 4° C.

Yield: 13.8 mg ovomucoid/ml carrier.

EXAMPLE 5.7

The activation of 1 ml pearl cellulose follows as described in Example 5.1. For the coupling, 1.3 ml concanavalin A-solution (10 mg concanavalin A) in 0.1M Na-tetraborate buffer pH8 are added. Then follows agitation for five hours at room temperature.

Yield: 6.7 mg ConA/ml carrier. described above, or two or more together, may also find a useful application in other types of syntheses different from the type described above.

While the invention has been illustrated and described as embodied in N-(chlorocarbonyloxy)-5-norbornene-2,3-dicarboximide, processes for its production and its use, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

It is claimed as new and deserves to be protected by Letters Patent as set forth in the appended claims.

We claim:

1. N-(chlorocarbonyloxy)-5-norbornene-2,3-dicarboximide I.

* * * * *